United States Patent
Daley et al.

(10) Patent No.: US 6,410,823 B1
(45) Date of Patent: *Jun. 25, 2002

(54) APERTURED FILM COVERS WITH LOCALIZED WETTABILITY AND METHOD FOR MAKING THE SAME

(75) Inventors: Michael Allen Daley, Alpharetta; Mark Bruce Majors, Cumming; Ali Yahiaoui, Roswell; Arthur Edward Garavaglia, Alpharetta; Michael David Powers, Canton; David Wayne Primm, Cumming; Tamara Lee Mace, Doraville; Nancy Donaldson Kollin, Roswell; Gregory Alan Zelazoski, Kennesaw; Jon Edward Tinsley, Roswell; Jaime Braverman, Atlanta, all of GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/108,096

(22) Filed: Jun. 30, 1998

(51) Int. Cl.[7] .............................................. A61F 13/15
(52) U.S. Cl. ................................. 604/383; 604/385.01
(58) Field of Search .............................. 604/383, 378, 604/385.01; 428/131–140

(56) References Cited

U.S. PATENT DOCUMENTS

| | | |
|---|---|---|
| 3,730,184 A | 5/1973 | Mesek |
| 3,837,343 A | 9/1974 | Mesek |
| 4,073,852 A | 2/1978 | Mesek |
| 4,324,246 A | 4/1982 | Mullane et al. |
| 4,351,784 A | 9/1982 | Thomas et al. |
| 4,456,570 A | 6/1984 | Thomas et al. |
| 4,535,020 A | 8/1985 | Thomas et al. |
| 4,735,843 A | 4/1988 | Noda |
| 4,755,413 A | 7/1988 | Morris |
| 4,758,297 A | 7/1988 | Calligarich |
| 4,820,294 A | 4/1989 | Morris |
| 5,520,875 A * | 5/1996 | Wnuk et al. ................. 264/504 |
| 5,648,142 A | 7/1997 | Phillips |
| 5,658,639 A | 8/1997 | Curro et al. |
| 5,700,872 A | 12/1997 | Wang et al. |

FOREIGN PATENT DOCUMENTS

| | | | |
|---|---|---|---|
| EP | 359 501 | 3/1990 | ........... A61F/13/15 |
| EP | 749 740 | 12/1996 | ........... A61F/13/15 |
| EP | 761 189 | 3/1997 | ........... A61F/13/15 |
| WO | 93/09741 | 5/1993 | ........... A61F/13/15 |
| WO | 98/10726 | 3/1998 | ........... A61F/13/15 |
| WO | 98/20826 | 5/1998 | ........... A61F/13/62 |
| WO | 98/22068 | 5/1998 | ........... A61F/13/15 |

* cited by examiner

*Primary Examiner*—Dennis Ruhl
(74) *Attorney, Agent, or Firm*—Pauley Petersen Kinne & Erickson

(57) ABSTRACT

A film cover for use in absorbent materials such as feminine care products, surgical drapes, fenestration reinforcement, absorbent pads and the like including a polymeric film having a top planar surface and a bottom planar surface and forming a plurality of apertures, at least a portion of which have an aperture region having a higher wettability than a portion of the top planar surface of the polymeric film.

14 Claims, 2 Drawing Sheets

APERTURED FILM COVERS WITH LOCALIZED WETTABILITY AND METHOD FOR MAKING THE SAME

BACKGROUND OF THE INVENTION

1. Field of the Invention

This invention relates to a topsheet or cover material for absorbent articles or materials, for example, feminine care products such as sanitary pads or napkins, and the like, surgical drapes, fenestration reinforcement, absorbent pads and similar materials. More particularly, this invention relates to apertured film covers which provide rapid fluid intake and low cover staining compared to conventional cover materials.

Films have been traditionally used to provide barrier properties in limited use or disposable items. By limited use or disposable, we mean that the product and/or component is used only a small number of times, or possibly only once, before being discarded. Examples of such products include, but are not limited to, surgical and healthcare related products such as surgical drapes and gowns, disposable absorbent pads used, for example in the meat industry, and personal care absorbent products such as diapers, training pants, incontinence garments, sanitary napkins, bandages, wipes and the like.

In protective apparel, such as hospital gowns, films are used to prevent cross exchange of microorganisms between the wearer and the patient. Although these films are generally effective barriers with respect to water vapor and the like, they are not aesthetically pleasing because their surfaces are smooth and either feel slick or tacky, and they are visually unappealing, making them less desirable in apparel applications and other uses where they are in contact with human skin. A primary purpose of the film in such laminates is to provide barrier properties. However, there is also a need that such laminates be fluid transmissive so that they can transmit fluids in a direction away from the fluid source. Similar requirements exist for absorbent materials such as absorbent pads used, for example, in the meat industry and absorbent materials used for fenestration reinforcement.

2. Description of Prior Art

Most absorbent articles include a cover material, an absorbent core, and some type of backing material which is generally liquid impervious to help prevent leakage. Types of cover materials generally fall into two main groups based, at least in part upon performance and aesthetic preferences. In the area of feminine care and sanitary napkins, the market is polarized into two segments, women who prefer clean and dry apertured film covers and women who prefer soft, cloth-like nonwoven covers. The advantage of apertured film covers for sanitary napkins is that they provide a relatively clean and dry surface as menses or menstrual discharge tends to pass through the apertured film layer and into the interior of the absorbent product. A drawback, however, is that such apertured film layers do not provide the degree of softness and comfort that a nonwoven cover material can provide. An additional drawback is the smooth, slick, non-cloth-like feel that is characteristic of many apertured films. Nonwoven-based cover materials, on the other hand, are very soft and cloth-like in feel but tend to retain more of the menses at or just below the surface of the cover material which, in turn, makes the product suffer from the standpoint of properties such as cleanliness and dryness. The difference in functionality is a direct result of the structure of nonwovens, including small average pore size and nonuniform pore size distribution.

Cover sheet materials are utilized for the transport of bodily fluids into the absorbent core of personal care absorbent articles and, thus, materials used for cover sheet applications must manage distinctly different body excretions, depending upon the application and the product type. Some products must manage fluids, such as urine, while others must manage viscoelastic fluids, such as menstrual discharge and fecal matter. The management of viscoelastic menstrual discharge by cover sheet materials for feminine care products is exacerbated by the variations in composition and rheology over a broad range of elasticity. Fluid management in feminine care applications requires control of absorption of bodily fluids, control of fluid retention in the cover, control of stain size and intensity, control of rewet of fluid back to the surface, and control of the release of fluid to the absorbent core.

There are basically three major classes of cover systems which have been developed to manage these fluids: nonwovens, apertured films, and composites of films and/or nonwovens. The characteristics of an ideal cover system include the capability of immediate fluid intake, no rewet of fluid back to the surface, no fluid retention in the cover, non-staining, and complete desorption of the fluid to the absorbent core.

Apertured film covers have been defined in the art for use in feminine care applications. Much of the art teaches the use of hydrophobic polyolefin film covers comprised of polyethylene as the base sheet. One drawback of these covers is that they tend to have poor fluid intake unless the pore diameter is large. However, as the pore size increases, the cover will have a tendency towards higher rewet and may detract from visual signal to the consumer. Also known in the art is the use of hydrophilic treatments which are topically applied to the surface to promote rapid fluid intake. However, these cover materials tend to display high rewet high fluid retention, and a lot of staining. Thus, an optimal cover is one that has rapid fluid intake coupled with low cover staining and fluid retention. One means for attaining this feature is an apertured film having wettable apertures and a hydrophobic top surface. Numerous means for attaining this feature are described in the prior art, but most of these means are unfeasible to process commercially, fugitive in nature, not regenerative, lacking control as to surfactant location, or limited to surfactant types. See, for example, U.S. Pat. No. 4,755,413 and U.S. Pat. No. 4,820,294 to Morris which teach an apertured plastic film wherein the edges of the apertures are coated with a hydrophilic material and a method of manufacture in which the apertures are formed by pin aperturing and the hydrophilic material is applied to the edges of the apertures as the pins are withdrawn. Because the hydrophilic material is applied in this manner, it is not possible to accurately control the final disposition of the hydrophilic material on the apertured plastic film. See also, U.S. Pat. No. 4,735,843 to Noda. This invention defines a simple means for attaining an apertured film with apertured regions of a higher surface energy than the top surface as well as a means for controlling and maintaining the surface energy or the distribution of surface energy in the pore or on the surface.

SUMMARY OF THE INVENTION

It is one object of this invention to provide a method for producing apertured film covers for use in a fluid absorbent material such as feminine care products, surgical drapes, fenestration reinforcement, absorbent pads and the like having aperture regions having a higher wettability than at least a portion of the top surface thereof.

It is another object of this invention to provide a method for producing apertured film covers for use in a fluid absorbent material which provides a means for controlling the surface energy (wettability) or the distribution of surface energy in the apertures and/or an area of the film cover immediately surrounding the apertures and/or on the surface of the film cover.

These and other objects of this invention are achieved by a method for producing a film cover for use in a fluid absorbent material comprising the steps of forming a polymeric film having a surfactant reservoir, a top planar surface and a bottom planar surface and forming a plurality of apertures in the polymeric film whereby at least a portion of the apertures have an aperture region having a higher surface energy or wettability than at least a portion of the top planar surface of the polymeric film. In accordance with one preferred embodiment of this invention, the polymeric film comprises a plurality of layers, at least one of which comprises a polymer selected from the group consisting of virgin polymer, polymer blends, copolymers, polymers with fillers, polymers with additives, and mixtures thereof and another of which comprises a blend of a polymer selected from the group consisting of virgin polymer, polymer blends, copolymers, polymers with fillers, polymers with additives, and mixtures thereof and a plurality of pellets, which plurality of pellets are formed by internally compounding at least one surfactant into a polymeric resin and extruding the polymeric resin into pellets.

In accordance with one embodiment, the polymeric film comprises a plurality of layers, at least one of which comprises a polymer selected from the group consisting of virgin polymer, polymer blends, copolymers, polymers with fillers, polymers with additives, and mixtures thereof and another of which comprises a polymer selected from the group consisting of virgin polymer, polymer blends, copolymers, polymers with fillers, polymers with additives, and mixtures thereof and at least one surfactant, which is added by direct addition to a melt during processing.

Suitable means for aperturing of the polymeric film include pin aperturing, slitting and stretching of the polymeric film, and vacuum aperturing. Aperturing in accordance with the method of this invention produces a plurality of apertures, each of which comprises a peripheral wall, or flap, around at least a portion of a periphery of each aperture, which peripheral wall extends from a bottom surface of the polymeric film.

In accordance with one embodiment of this invention, the polymeric film is formed from a polymeric material comprising a plurality of spheres, or microcapsules, of a surfactant and the apertures are formed by electric discharge means or mechanical means whereby the spheres of surfactant are ruptured, thereby rendering edges of the apertures wettable.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Figure 1:
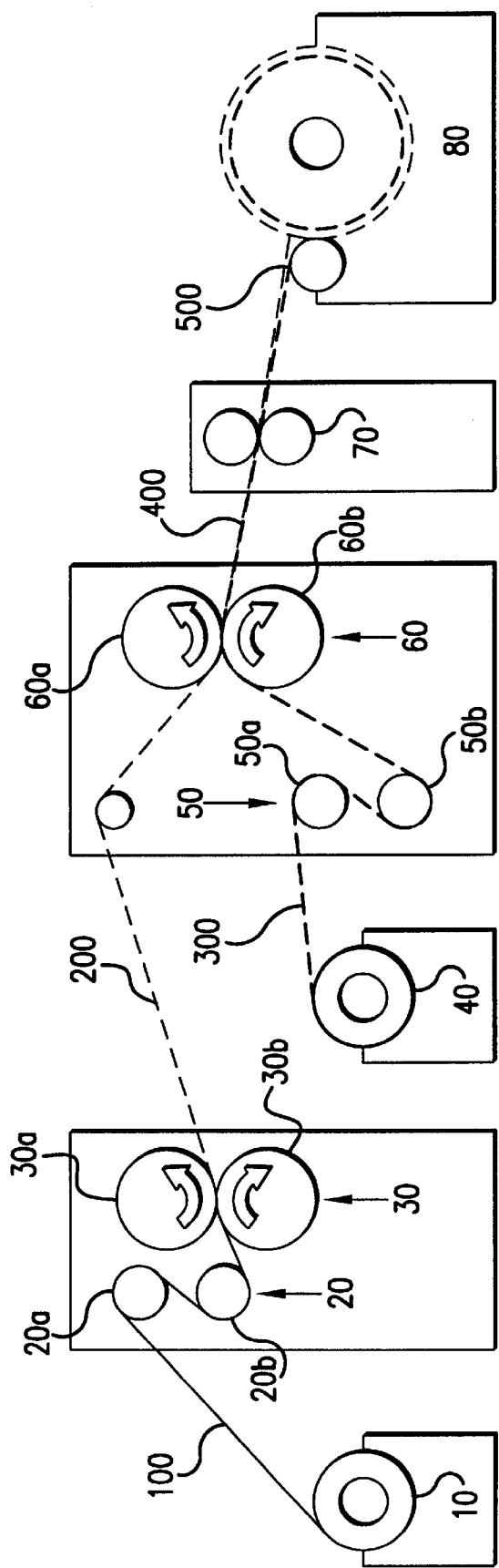
FIG. 1 is a schematic diagram showing a process for producing a film cover for use in a fluid absorbent material in accordance with one embodiment of this invention.

A critical element in the fluid handling properties of materials used in fluid absorbent materials such as personal care absorbent products is surface wettability. For example, the capillary forces that drive fluid intake and wicking derive from the interfacial free energies at the fluid/air/material interfaces. Wettability is a gauge of the surface free energy of the solid phase. A classic method for measuring the wettability of the surface is the contact angle technique in which a droplet of fluid is placed on a flat surface and the angle at which the droplet intercepts the surface is measured. The equation relating contact angle ($\theta$) to interfacial free energy (g) is known as Young's equation, that is:

$$g_{SV} = g_{SL} + g_{LV} \cos\theta$$

where SV, SL, and LV refer to the surface/vapor, surface/liquid and liquid/vapor interfaces, respectively. This equation is true for fluids at equilibrium, that is not moving, on a surface. As fluids move across a surface, the contact angle at the fluid front, known as the advancing contact angle, $\theta_{ADV}$, is increased slightly from the equilibrium value and the contact angle at the back edge of the fluid, known as the receding contact angle, $\theta_{REC}$, is decreased slightly from the equilibrium value.

Wettability of the surface is governed by the chemical structure and condition of the surface. When an initial fluid insult contacts and moves into a cover material, the fluid contacts a "dry" surface with wettability controlled by the inherent chemical structure of the surface. For surfaces in contact with fluid or which have had prior fluid contact, the effect of advancing and receding contact angles on fluid movement are often complicated by the fact that these surfaces are altered by the fluid contact For example, changes in the receding contact angle, $\theta_{REC}$, can be caused by the removal of fugitive surface treatments responsible for wettability (which could decrease wettability and increase the contact angle) or by responses of the surface to the insult fluid, such as surface hydration and protein deposition (both of which would increase wettability and decrease the contact angle). These effects can take place in the time frame of fractions of a second, as is frequently the case for protein deposition, or many minutes, as usually occurs for surface hydration or surfactant coating detachment.

A film cover for use in a fluid absorbent material in accordance with this invention comprises a polymeric film having a surfactant reservoir, a top planar surface and a bottom planar surface, and forming a plurality of apertures, at least a portion of which have an aperture region having a higher surface energy or wettability than at least a portion of the top planar surface. By the term "aperture region", we mean the peripheral wall of the aperture, a portion of the top planar surface immediately surrounding the aperture, and any portions of the peripheral wall extending below the bottom planar surface. The surfactant reservoir within the polymeric film can be produced in any manner which enables the higher surface energy of the aperture regions to be maintained, even after being subjected to multiple fluid insults. At least a portion of the apertures, in accordance with one embodiment, comprise a peripheral wall surrounding at least a portion of each of the apertures and extending from the bottom planar surface of the polymeric film. In accordance with one embodiment of this invention, the polymeric film comprises a plurality of layers, at least one of which comprises a surfactant disposed therein. In accordance with another embodiment of this invention, a surfactant, or wetting agent, is applied to at least a portion of the bottom planar surface of the polymeric film in order to promote wettability. In accordance with a particularly preferred embodiment, the surfactant is present in an amount in an add-on range of about 0.1 to about 3.0 weight percent.

Apertured film covers produced in accordance with the method of this invention have an open area in the range of about 10% to about 35% and a pore size in the range of about 100 to about 700 microns equivalent circular diameter (ECD). In accordance with the embodiment of this invention wherein the surfactant is disposed within at least one layer of a multilayer polymeric film comprising the apertured film cover of this invention, the layer comprising the surfactant has a thickness in the range of about 10% to about 90% of the total thickness of the apertured film.

In accordance with one embodiment of the method of this invention, surfactants are internally compounded at a given level into a polymer resin and extruded into pellets. ABA cast films are prepared with a polymer in the A layers and blends of polymer and pellets with internal surfactants in the B layer. In this manner, a film is prepared with an internal surfactant in the middle layer. It will, however, be apparent to those skilled in the art that the surfactant can be positioned in the top layer or in a number of other positions within a multilayer polymeric film using two layers (AB films), five layers (ABCBA films), etc. Alternatively, films can be prepared with surfactant in a given layer through a number of other means. For example, surfactant can be added to a layer by direct addition to the melt during processing.

The film is apertured by any number of means including pin aperturing, slitting and stretching, and vacuum aperturing. In accordance with one embodiment, the film is pin apertured by passing it through a heated nip where the differential speeds between the pattern roll and the anvil roll create apertures as defined by the process conditions and the embossing pattern. The process of aperturing the film using a heated roll causes a portion of the B layer containing the internal surfactant to be exposed. In addition, heat from the pins on the pattern roll causes the internal surfactant to diffuse from the bulk to the aperture surface from a point of higher concentration to a point of lower concentration. As a result, wettable apertures are attained. The level of wettability in and around the aperture is controllable by three means: (1) surfactant chemistry, (2) thickness of the layer containing the internal surfactant (for example, the B layer), and (3) the concentration of the surfactant within the given layer.

More particularly, surfactant chemistry, that is, the size and shape of the molecule comprising the surfactant as well as the structure of the polymer into which the suffactant is internally compounded can control the diffusion of the surfactant through the polymer matrix. In particular, a small molecule will diffuse more easily through a polymer matrix than a larger molecule, resulting in an aperture having more treatment along its length. A surfactant which is at a higher concentration will tend to diffuse more readily to the surface than one at lower concentrations, producing a large number of surfactant molecules at the aperture surface. At higher concentrations, the treatment may cause the aperture to be wettable (hydrophilic) and may even migrate to regions of the top surface immediately surrounding the aperture while still maintaining the remaining portions of the top surface between apertures hydrophobic. The B layer thickness may also be controlled to control wettability within the aperture or around the aperture on the surface.

Figure 3:
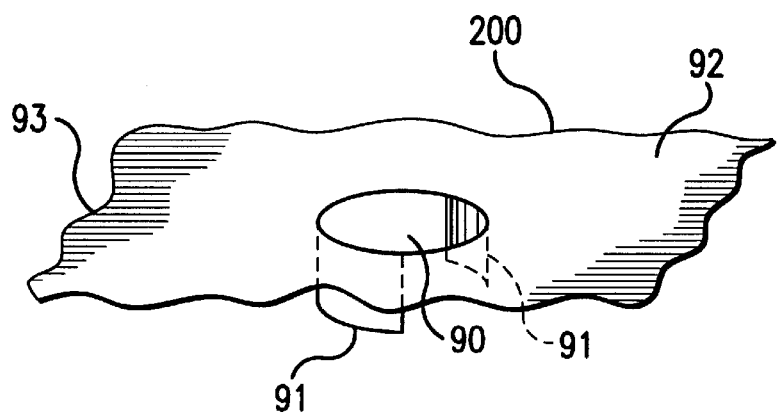
FIG. 3 is a schematic diagram of a portion of an apertured film in accordance with one embodiment of this invention.

Another method for producing apertured film covers having higher surface energy on and around the apertures as compared to the top surface of the film cover in accordance with one embodiment of this invention, although producing less favorable results, comprises mechanically aperturing a polyethylene film so as to produce an apertured film 200 as shown in FIG. 3 comprising a top surface 92 containing the top opening of the mechanical aperture 90 and a connected trailing flap 91, or peripheral wall, around the periphery of the aperture and extending from the bottom planar surface 93 of the polymeric film. Thereafter, a surfactant, or wetting agent, is applied to the bottom side of the film by means of a transfer coating. The preferred treatment add-on range is in the range of about 0.1 to about 3.0% by weight. The amount and placement of the surfactant can be varied by varying the process conditions. In accordance with one embodiment, only the flap portion is treated with the surfactant. In accordance with another embodiment, the surfactant is applied such that the inner wall of the aperture also becomes coated and wettable.

In accordance with one embodiment of this invention, the polymeric film comprises a plurality of spheres containing an appropriate surfactant. The polymeric film is then perforated using electrical discharge or mechanical means. As a result of the perforation, or aperturing, process, the edges of the apertures are rendered wettable when the electrical discharge or mechanical means rupture the microencapsulated surfactant in the film.

EXAMPLE 1

Surfactants (Atmer, available from ICI Americas, Inc., Wilmington, Del.; Ahcovel, available from ICI Americas, Inc.; Masil, available from PPG Industries, Inc., Gurnee, Ill.; and MAPEG, available from PPG Industries, Inc.) were internally compounded into polyethylene resin and extruded into pellets having the following formulations:

Atmer 8147 Concentrate—80% polyethylene/20% Atmer 8147;

Ahcovel Base N-62 Concentrate—90% Rexene 1058/ 10% Ahcovel Based N-62;

Masil SF-19 Concentrate—90% Rexene 1058/10% Masil SF-19;

MAPEG 400 ML Concentrate—90% Rexene 1058/10% MAPEG 400 ML.

These compounded resins were then blended with additional resins and used to form the B layer of an ABA cast film. Cast films were prepared based upon the following formulations using conventional melt extrusion, cast film techniques.

| Control | 94% Rexene 1058, 6% Ampacet 110359 | |
|---|---|---|
| Atmer Low | 30% | Layer A - (94% Rexene 1058, 6% Ampacet 110359); |
| | 40% | Layer B - (93.5% Rexene 1058, 0.5% Atmer 8174 Concentrate (20% in polyethylene), 6% Ampacet 110359); |
| | 30% | Layer A - (94% Rexene 1058, 6% Ampacet 110359) |
| Atmer High | 30% | Layer A - (94% Rexene 1058, 6% Ampacet 110359); |
| | 40% | Layer B - (91.5% Rexene 1058, 2.5% Atmer 8174 Concentrate (20% in polyethylene), 6% Ampacet 110359); |
| | 30% | Layer A - (94% Rexene 1058, 6% Ampacet 110359) |
| MAPEG Low | 30% | Layer A - (94% Rexene 1058, 6% Ampacet 110359); |
| | 40% | Layer B - (93% Rexene 1058, 1% MAPEG 400 ML Concentrate (10% in Rexene 1058), 6% Ampacet 110359); |
| | 30% | Layer A - (94% Rexene 1058, 6% Ampacet 110359) |

-continued

| Control | 94% Rexene 1058, 6% Ampacet 110359 |
|---|---|
| MAPEG High | 30% Layer A - (94% Rexene 1058, 6% Ampacet 110359); |
| | 40% Layer B - (89% Rexene 1058, 5% MAPEG 400 ML Concentrate (10% in Rexene 1058), 6% Ampacet 110359); |
| | 30% Layer A - (94% Rexene 1058, 6% Ampacet 110359) |
| Ahcovel Low | 30% Layer A - (94% Rexene 1058, 6% Ampacet 110359); |
| | 40% Layer B - (93% Rexene 1058, 1% Ahcovel Base N-62 Concentrate (10% in Rexene 1058), 6% Ampacet 110359); |
| | 30% Layer A - (94% Rexene 1058, 6% Ampacet 110359) |

These films were then apertured in accordance with the process shown in FIG. 1. In particular, the films were apertured mechanically in nip 30. The aperturing process comprises controlling the feed rate of the film 100 separate from the aperturing rate. The feed and the aperturing rate are controlled by the drive system 20. The aperturing rate is controlled by the rotation rate of the rolls in the aperturing nip 30, pattern roll 30a and anvil roll 30b. The speed of the film 100 is slower than the peripheral speed of pattern roll 30a and faster than the peripheral speed of anvil roll 30b.

Film 100 is apertured under tension to minimize wrinkling of the film from a driven unwind 10 slower than the speed that drive system 20 and idler rolls (not shown) pull the film 100. The drive unit comprises "S" wrapping the film 100 between a driven rubber roll 20a and a steel roll 20b to control the entrance speed of the film into aperturing nip 30. Pattern roll 30a and anvil roll 30b contact one another and form nip 30 therebetween. Pattern roll 30a and anvil roll 30b rotate in opposite directions. Each of pattern roll 30a and anvil roll 30b is driven separately. Peripheral speed of pattern roll 30a is set at about 1.3–1.4 times the peripheral speed of anvil roll 30b.

For our work, film 100 was apertured at a speed of 100 feet per minute. Each of pattern roll 30a and anvil roll 30b was made from stainless steel and had an outside diameter of about 24 inches, The rolls were maintained at different temperatures using an internal hot oil system, pattern roll 30a being maintained at a temperature of about 255° F. and anvil roll 30b being maintained at a temperature of about 228° F. Anvil roll 30b had a smooth finish while pattern roll 30a had a plurality of pins positioned to give a desired pattern. The desired pattern had a density of about 93.5 pins per square centimeter (580–603 pins/inches$^2$) and a total contact area of about 37–46%. Each pin had a height of about 0.48 millimeters (0.01–0.022 inches), was tapered about 10°, and was circular in cross section. Because the pins had an apex diameter of about 0.73 millimeters (0.0286 inches), the surface area of the apex was about 0.40 millimeters$^2$ (0.00066 inches$^2$).

As film 100 enters nip 30, it is apertured through the application of heat, shear and pressure by penetrating pins which extend completely through the thickness of film 100. Shear is created by running the pattern roll 30a faster than the anvil roll 30b. The apertured film 200 exits nip 30 under tension and can be directed around an idler roll (not shown) to keep the apertured film 200 from wrinkling as it is separated from pattern roll 30a. These process conditions produce an apertured film having an open area of approximately 28% with an equivalent-circular diameter (ECD) of approximately 600 microns.

EXAMPLE 2

In this example, the apertured films of Example 1 were thermally bonded to a nonwoven web to form apertured films/nonwoven laminates.

The nonwoven web used in this example was produced by through-air bonding a carded web. It will, however, be apparent to those skilled in the art that other nonwoven materials may also be employed. This particular nonwoven web was made of bicomponent fibers from Chisso Corporation. Chisso applies a proprietary finish, known as "HR6" on the fiber which renders the fiber wettable. The fibers were in a sheath core configuration. The core of the fiber was polypropylene, which constituted about 50% by weight of the fiber, and the sheath was low density polyethylene (LDPE), which constituted the remaining 50% by weight of the fiber. These fibers were about 51 millimeters (2.00 inches) in length and 10 denier. In particular, this nonwoven web, described as a TABCW, had a density of about 0.0182 g/cc and a permeability of 15,000 Darcys.

The laminate was formed by thermomechanically point bonding the apertured film to the nonwoven TABCW. With reference again to FIG. 1, the bonding took place inside a nip which consisted of two heated bonding rolls rotating in opposite directions. In particular, laminating nip 60 was comprised of a pattern roll 60a and an anvil roll 60b. The two rolls contact one another to form nip 60 therebetween. Each of the rolls was driven separately such that the peripheral speed of pattern roll 60a matched the peripheral speed of anvil roll 60b. Pattern roll 60a and anvil roll 60b were made from stainless steel and had an outside diameter of about 24 inches (70 cm). The rolls were maintained at different temperatures by internal hot oil.

Anvil roll 60b had a smooth finish, while pattern roll 60a had a plurality of pins which were positioned to give a desired pattern. The desired pattern had a density of about 5.2 pins per square centimeter (33.6 pins/inches$^2$) and a total contact area of about 8–12%. Each pin had a height of about 2.4 mm (0.095 inches), was tapered about 20°, and was circular in cross section. The pins had an apex diameter of about 1.6 mm (0.065 inches). Both film 200 and nonwoven web 300 enter laminating nip 60 under tension. While nonwoven web 300 is under tension, it stretches approximately 3–12% relative to film 200. Tension in nonwoven web 300 is maintained by unwinding nonwoven web 300 from unwind 40 slower than the speed that drive system unit 50 and idler rolls (not shown) pull nonwoven web 300. Drive unit 50 comprises "S" wrapping a film between driven rubber roll 50a and steel roll 50b for the purpose of controlling entrance speed of nonwoven web 300 into laminating nip 60. Tension in apertured film 200 is maintained by laminating nip 60 and idler rolls (not shown).

Bonding takes place as film 200 and nonwoven web 300 passes between the rolls in nip 60. Nonwoven web 300 and film 200 speed matches the peripheral speeds of pattern roll 60a and anvil roll 60b. In particular, this speed did not exceed 100 feet per minute. As film 200 and nonwoven web 300 passed through nip 60, film 200 was laminated through the application of heat and pressure.

EXAMPLE 3

Fluid intake time, rewet value, and stain size were measured for apertured films with wettability gradients as a function of treatment type and concentration and were compared to an apertured film with no wettability gradients. The apertured film covers were evaluated over a standard two layer absorbent core. The top layer of the absorbent core (closest to the cover) was a 90% Coosa 0054/10% Hoechst-Celanese T-255 binder, 100 gsm (grams per square meter), 0.1 g/cc airlaid web, and the bottom layer of the absorbent core was a 90% Coosa 0054/10% Hoechst-Celanese T-255 binder, 200 gsm, 0.2 g/cc airlaid web. The results are shown in Table 1 hereinbelow.

TABLE 1

Fluid Management Properties for Apertured Film Covers

| Sample | Intake Time (s) | Rewet (grams) | Average Stain Size (mm$^2$) |
|---|---|---|---|
| Control | 25 | 0.12 | 563 |
| Atmer-Low | 16 | 0.26 | 324 |
| Atmer-High | 13 | 0.33 | 642 |
| MAPEG-Low | 14 | 0.15 | 544 |
| MAPEG-High | 12 | 0.28 | 1077 |
| Ahcovel-Low | 13 | 0.29 | 407 |

As can be seen from Table 1, the fluid intake time for the apertured film covers produced in accordance with the method of this invention decreased with the addition of a suffactant treatment primarily in and/or around the apertures compared to the control film cover. With increased surfactant treatment concentration, fluid intake time decreased only modestly. Stain size decreased significantly with decreased surfactant treatment level due to better fluid intake and less fluid retention and wicking on the film cover. Presumably at higher treatment concentration, the treatment migrates to the top surface and provides high fluid retention and wicking as noted by the large stain size for Atmer-High and MAPEG-High. Covers with low levels of treatment in and/or around the apertures demonstrated lower levels of staining compared to the control film cover. Also, as can be seen, rewet properties generally increased, but can be minimized with treatment type and concentration as seen for the MAPEG-low sample apertured film cover. Rewet in this case is similar to the control film cover.

Table 2 shows fluid intake time and rewet values for apertured film/nonwoven laminates produced in accordance with the method of this invention compared to a control laminate. In particular, the control laminate with no treatment is compared to an apertured film/nonwoven laminate having high wettability localized in and/or around the apertures. The apertured film covers were evaluated over a standard two layer absorbent core. The top layer of the absorbent core (closest to the cover) was a 90% Coosa 0054/10% Hoechst-Celanese T-255 binder, 100 gsm, 0.1 g/cc airlaid web, and the bottom layer of the absorbent core was a 90% Coosa 0054/10% Hoechst-Celanese T-255 binder, 200 gsm, 0.2 g/cc airlaid web. As shown in Table 2, the presence of a surfactant treatment in and/or around the apertures has limited impact on the fluid intake and rewet properties of the material. In addition, the presence of a nonwoven web laminated to any apertured film substantially reduces fluid intake time and rewet compared to the apertured films by themselves.

TABLE 2

Fluid Management for Apertured Film Nonwoven Composites

| Sample | Intake Time(s) | Rewet (grams) |
|---|---|---|
| Control - Laminate | 7 | 0.03 |
| Atmer-High - Laminate | 6 | 0.04 |

TEST METHODS

A. Percent Open and Pore Size Measurement On An Apertured Film

A piece of apertured film (approximately 4 inches by 6 inches) is laid flat onto an auto-stage, for example, Mertzshauser, Inc., of a microscope, for example, Olympus Model BH-2. The film is normally laid such that the "cone" or "flap" surface is face down on the stage. In order to ensure that the film stays in place and remains flat on the stage surface, that is, free of wrinkles, a ¼ inch thick glass plate is placed on top of the film. A 1× or 2× objective lens is then positioned in place. Transmitted light is used with a sub-stage condenser to illuminate the apertures in the film. A video camera that is interfaced to an image analysis (IA) system is mounted on top of the microscope. The image analysis system is then used to acquire images and make measurements from multiple regions on the film. The image analysis system uses software that is uniquely written to move the microscope's auto-stage, acquire images, process images, and make open area and pore size measurements. Often, the stage is moved over a rectangular grid to perform measurements on multiple fields-of-view. Non-apertured areas normally appear nearly "black" for opaque film while detected open areas will normally appear nearly "white". The measurement of percent open area is defined as the percentage of area detected where transmitted light passes unhindered through the apertures. There is 1% open value obtained per field-of-view. For apertured films, pore size is normally measured as equivalent-circular diameter (ECD) and is derived from the following equation:

$$ECD = (4 \times Area/\pi)^{1/2}$$

Because multiple apertures are normally present in each field of view, multiple ECD values are obtained for each field of view. Typically, percent open area and equivalent-circular diameter pore size data are reported as averages obtained from multiple fields-of-view acquired from 2–4 individual samples.

B. Rate Block Intake Test

Figure 2:
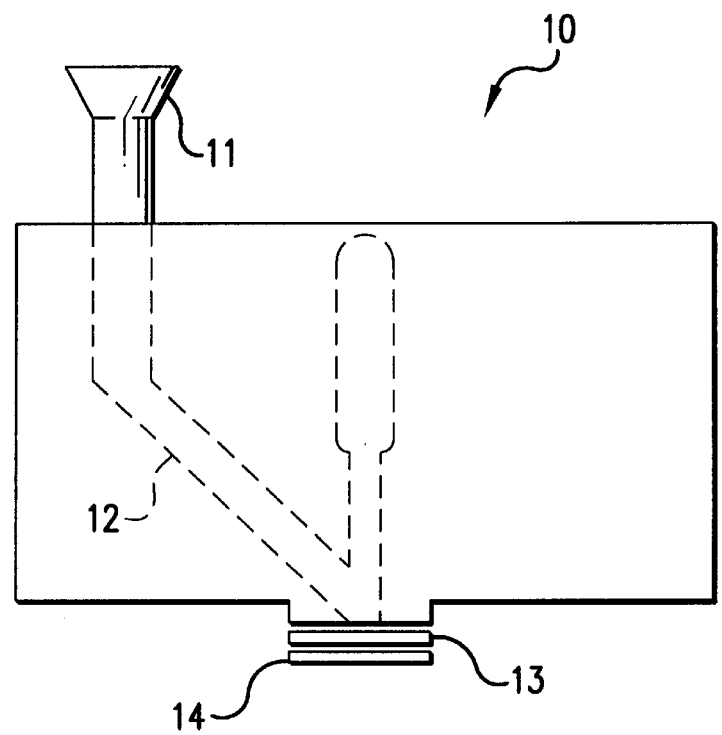
FIG. 2 is a diagram of a test apparatus for determining the fluid intake time of a fluid into a material.

This test is used to determine the intake time of a known quantity of fluid into a material and/or material system. The test apparatus consists of a rate block 10 as shown in FIG. 2. A 4"×4" piece of each of the absorbents 14 and cover 13 are die cut. The specific covers are described in the specific examples. The absorbent used for these studies was standard and consisted of a top piece (closest to the cover) of a 90% Coosa 0054/10% Hoechst-Celanese T-255 binder, 100 gsm, 0.1 g/cc airlaid web and a bottom piece which was a 90% Coosa/10% Hoechst-Celanese T-255 binder, 200 gsm, 0.2 g/cc airlaid web. The cover 13 was placed over the two pieces of absorbent 14 and the rate block 10 was placed on top of the two materials. 2 mL of a menses stimulant was delivered into the test apparatus film 11 and a timer started. The fluid moved from the funnel 11 into a channel 12 where it was delivered to the material or material system. The timer was stopped when all the fluid was absorbed into the material or material system as observed from the chamber in the test apparatus. The intake time for a known quantity of known fluid was recorded for a given material or material system. This value is a measure of a material or material systems absorbency. Typically, five to ten repetitions were performed, and average intake time was determined.

C. Rewet Test

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and, thus, a dryer product. In considering rewet, three properties are important: (1) intake, if the material/system does not have good intake then fluid can rewet, (2) ability of absorbent to hold fluid (the more the absorbent holds on to the fluid, the less is available for rewet), and (3) flowback, the more the cover prohibits fluid from coming back through the cover, the lower the rewet. In our case, we evaluated cover systems where the absorbent was maintained constant and, thus, we were only concerned with properties (1) and (3), intake and flowback, respectively.

A 4"×4" piece of absorbent and cover was die cut. The absorbent used for these studies was standard and consisted of a top piece (closest to the cover) of a 90% Coosa 0054/10% Hoechst-Celanese T-255 binder, 100 gsm, 0.1 g/cc airlaid web and a bottom piece which was a 90% Coosa/10% Hoechst-Celanese T-255 binder, 200 gsm, 0.2 g/cc airlaid web. The cover was placed over the two pieces of absorbent and the rate block was placed on top of the two materials. In this test, 2 mL of menses simulant are insulted into the rate block apparatus and are allowed to absorb into a 4"×4" sample of the cover material which is placed on top of a 4"×4"absorbent piece. The fluid is allowed to interact with the system for one minute and the rate block rests on top of the materials. The material system cover and absorbent are placed onto a bag filled with fluid. A piece of blotter paper is weighed and placed on top of the material system. The bag is traversed vertically until it comes into contact with an acrylic plate above it, thus pressing the whole material system against the plate blotter paper side first. The system is pressed against the acrylic plate until a total pressure of 1 psi is applied. The pressure is held fixed for three minutes, after which the pressure is removed and the blotter paper is weighed. The blotter paper retains any fluid that was transferred to it from the cover/absorbent system. The difference in weight between the original blotter and the blotter after the experiment is known as the "rewet" value. Typically, five to ten repetitions of this test were performed, and average rewet was determined.

D. Intake/Staining Test

An intake/staining test was developed which enables the stain size, intensity, and fluid retention in components to be observed with fluid flow rate and pressure. Menses simulant was used as the test fluid. A 4"×4" piece of absorbent and cover were die cut. The absorbent used for these tests was standard and consisted of a top piece (closest to the cover) of a 90% Coosa/10% Hoechst-Celanese T-255 binder, 100 gsm 0.1 g/cc airlaid web and a bottom of a 90% Coosa/10% Hoechst-Celanese T-255 binder, 200 gsm, 0.2 g/cc airlaid web. A material system, cover and absorbent cores measuring 4"×4", was placed underneath an acrylic plate with an ⅛ inch diameter hole bored into the center. A piece of ⅛ inch tubing was connected to the hole with a fitting. Menses simulant was delivered to the sample using a syringe pump at a specified rate and for a specified volume. The pump was programmed to deliver a total volume of 1 mL to the samples, where the samples were under pressures of 0 psi, 0.0078 psi, and 0.078 psi. These pressures were applied using a weight which was placed on top of the acrylic plates and distributed evenly. The flow rate of the pump was programmed to deliver fluid at a rate of 1 mL/sec. The stain size for the cover materials was measured manually, and the amount of fluid in each component of the system was measured by weight before and after absorption of the fluid.

The stain was evaluated qualitatively by comparison of samples. Staining information was recorded using a digital camera and could be further analyzed with image analysis.

Menses Simulant Preparation

"Menses simulant" is a material which simulates the viscoelastic and other properties of menses. To prepare the fluid, blood, such as defibrinated swine blood, is separated by centrifuge at 3000 rpm for 30 minutes, although other methods or speeds and times may be used if effective. The plasma is separated and stored separately, the buffy coat removed and discarded, and the packed red blood cells stored separately as well. Eggs, such as jumbo chicken eggs, are separated, the yoke and chalazae discarded, and the egg white retained The egg white is separated into thick and thin portions by straining the white through a 1000 micron nylon mesh for about three minutes, and the thinner portion discarded. Alternative mesh sizes may be used, and the time or method may be varied provided the viscosity is at least that required. The thick portion of egg white which was retained on the mesh is collected and drawn into 60 cc syringes which are then placed on a programmable syringe pump and the fluid homogenized by expelling and refilling the contents five times. In our case, the amount of homogenization was controlled by the syringe pump rate of about 100 ml/min, and the tubing inside diameter of about 0.12 inches. After homogenizing, the thick egg white has a viscosity of about 20 centipoise at 150 sec-1 and it is then centrifuged to remove debris and air bubbles. After centrifuging, 80 mL of the thick homogenized egg white, which contains ovomucin, is added to a 300 cc FENWAL Transfer Pack using a syringe. Then, 60 cc of the swine plasma is added to the transfer pack. The transfer pack is clamped, all air bubbles removed, and placed in a Stomacher lab blender in which it is blended at normal (or medium) speed for about two minutes. The transfer pack is then removed from the blender, 60 cc of swine red blood cells are added, and the contents mixed by hand kneading for about two minutes, or until the contents appear homogeneous. The final mixture has a red blood cell content of about 30 volume percent and generally is at least within the range of 28–32 volume percent for artificial menses. The amount of egg white is about 40 weight percent.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An absorbent material comprising:
   an absorbent core;
   a backing material which is substantially liquid impervious; and
   a cover material comprising a multi-layer polymeric film comprising at least a top layer and a bottom layer and having a top planar surface and a bottom planar surface and forming a plurality of apertures, at least a portion of said plurality of apertures having an aperture region having a higher wettability than a portion of said top planar surface, and a surfactant disposed in at least one layer of said multi-layer polymeric film other than said top layer whereby said higher wettability of said aperture region is maintained after contact by a fluid.

2. An absorbent material in accordance with claim 1, wherein a peripheral wall surrounds at least a portion of a periphery of said apertures and extends from said bottom planar surface.

3. An absorbent material in accordance with claim 2, wherein said surfactant is present in an amount in an add-on range of about 0.1 to 3.0 weight percent.

4. An absorbent material in accordance with claim 1, wherein said polymeric film is laminated to a nonwoven web material.

5. An absorbent material in accordance with claim 1, wherein said polymeric film has an open area in a range of about 10% to about 35%.

6. An absorbent material in accordance with claim 1, wherein said apertures have a size in a range of about 100 to about 700 microns (ECD).

7. An absorbent material in accordance with claim 1, wherein said at least one layer comprising said surfactant has a thickness in a range of about 10% to about 90% of said polymeric film.

8. A feminine care product comprising:

an absorbent core;

a backing material which is substantially liquid impervious; and a cover material comprising a multi-layer polymeric film comprising at least a top layer and a bottom layer and having a top planar surface and a bottom planar surface and forming a plurality of apertures, at least a portion of said plurality of apertures having an aperture region having a higher wettability than a portion of said top planar surface, and a surfactant disposed in at least one layer of said multi-layer polymeric film other than said top layer whereby said higher wettability of said aperture region is maintained after contact by a fluid.

9. A feminine care product in accordance with claim 8, wherein a peripheral wall surrounds at least a portion of a periphery of said apertures and extends from said bottom planar surface.

10. A feminine care product in accordance with claim 9, wherein said surfactant is present in an amount in an add-on range of about 0.1 to 3.0 weight percent.

11. A feminine care product in accordance with claim 8, wherein said polymeric film is laminated to a nonwoven web material.

12. A feminine care product in accordance with claim 8, wherein said polymeric film has an open area in a range of about 10% to about 35%.

13. A feminine care product in accordance with claim 8, wherein said apertures have a size in a range of about 100 to about 700 microns (ECD).

14. A feminine care product in accordance with claim 8, wherein said at least one layer comprising said surfactant has a thickness in a range of about 10% to about 90% of said polymeric film.

* * * * *